(12) United States Patent
Walzman

(10) Patent No.: US 10,857,335 B2
(45) Date of Patent: Dec. 8, 2020

(54) TEMPORARY BYPASS BALLOON CATHETER

(71) Applicant: Daniel E. Walzman, Bergenfield, NJ (US)

(72) Inventor: Daniel E. Walzman, Bergenfield, NJ (US)

(73) Assignee: Daniel Ezra Walzman, Bergenfield, NJ (US)

( * ) Notice: Subject to any disclaimer, the term of this patent is extended or adjusted under 35 U.S.C. 154(b) by 360 days.

(21) Appl. No.: 15/732,397

(22) Filed: Nov. 6, 2017

(65) Prior Publication Data

US 2018/0229010 A1 Aug. 16, 2018

Related U.S. Application Data

(60) Provisional application No. 62/600,134, filed on Feb. 13, 2017.

(51) Int. Cl.
*A61M 25/00* (2006.01)
*A61M 25/10* (2013.01)
*A61B 17/12* (2006.01)

(52) U.S. Cl.
CPC ..... *A61M 25/1025* (2013.01); *A61B 17/1204* (2013.01); *A61B 17/12036* (2013.01); *A61B 17/12109* (2013.01); *A61B 17/12113* (2013.01); *A61B 17/12136* (2013.01); *A61B 17/12186* (2013.01); *A61M 25/0029* (2013.01); *A61M 25/0071* (2013.01); *A61M 25/0084* (2013.01); *A61B 17/12031* (2013.01); *A61B 17/12045* (2013.01); *A61B 17/12195* (2013.01);

(Continued)

(58) Field of Classification Search
CPC .............. A61M 2025/1045; A61M 2025/1095
USPC ..................................................... 604/103.07
See application file for complete search history.

(56) References Cited

U.S. PATENT DOCUMENTS

| 4,183,102 A | | 1/1980 | Guiset |
| 4,309,994 A | * | 1/1982 | Grunwald ......... A61M 25/0026 604/28 |

(Continued)

FOREIGN PATENT DOCUMENTS

WO  WO 2005112823  12/2005

OTHER PUBLICATIONS

U.S. Appl. No. 15/258,877, filed Sep. 2016, Walzman.

*Primary Examiner* — Adam Marcetich

(57) ABSTRACT

A balloon catheter for treating aneurysms or other intraluminal target sites, having at least one bypass window through which blood flows temporarily and out at least one end hole, and a balloon mounted near the end hole, such that there is no need for repeated inflation/deflation cycles. The invention has an elongated tube, a balloon disposed between the most distal said window and said end hole, and at least two channels. A first channel passes from the proximal end of said tube to the bypass window to allow blood to flow into said window and out said end hole, and a second channel passing from the proximal end of said tube to said balloon to allow inflation material to enter said balloon.

In optional embodiments, a micro-catheter may pass through to treat a target site; the inner tube and balloon may be branched to facilitate treatment at a vascular branch, such as for a wide-neck aneurysm by balloon tamponade, a micro-catheter extension or other device passing through a bifurcation hole at the branch point.

16 Claims, 6 Drawing Sheets

(52) U.S. Cl.
CPC ............ *A61B 2017/1205* (2013.01); *A61M 2025/0042* (2013.01); *A61M 2025/0089* (2013.01); *A61M 2025/1052* (2013.01); *A61M 2025/1061* (2013.01); *A61M 2025/1095* (2013.01); *A61M 2025/1097* (2013.01)

(56) References Cited

U.S. PATENT DOCUMENTS

| | | | |
|---|---|---|---|
| 4,573,966 A | | 3/1986 | Weiki |
| 4,755,176 A | | 7/1988 | Patel |
| 4,784,638 A | | 11/1988 | Ghajar et al. |
| 4,795,427 A | | 1/1989 | Helzel |
| 4,944,745 A | * | 7/1990 | Sogard ............... A61M 25/104 604/103 |
| 4,968,306 A | | 11/1990 | Huss |
| 4,970,926 A | | 11/1990 | Ghajar et al. |
| 5,087,247 A | * | 2/1992 | Horn ................. A61M 25/104 604/103.1 |
| 5,147,302 A | | 9/1992 | Euteneuer et al. |
| 5,163,905 A | | 11/1992 | Don Michael |
| 5,167,628 A | | 12/1992 | Boyles |
| 5,180,387 A | | 1/1993 | Ghajar et al. |
| 5,344,402 A | * | 9/1994 | Crocker ............. A61M 25/1011 604/103.01 |
| 5,370,617 A | | 12/1994 | Sahota |
| 5,411,479 A | * | 5/1995 | Bodden ............... A61M 1/3621 604/101.03 |
| 5,460,610 A | | 10/1995 | Don Michael |
| 5,470,314 A | | 11/1995 | Walinsky |
| 5,542,925 A | * | 8/1996 | Orth ................... A61M 25/007 604/103.1 |
| 5,613,980 A | * | 3/1997 | Chauhan ............ A61M 25/1002 128/898 |
| 5,639,274 A | | 6/1997 | Fischell et al. |
| 5,669,924 A | * | 9/1997 | Shaknovich ............... A61F 2/07 604/101.04 |
| 5,720,735 A | * | 2/1998 | Dorros .................... A61F 2/90 604/284 |
| 5,769,828 A | * | 6/1998 | Jonkman ........... A61M 25/0012 604/508 |
| 5,800,407 A | | 9/1998 | Eldor |
| 5,830,181 A | * | 11/1998 | Thornton ............ A61M 25/104 604/102.01 |
| 5,840,066 A | | 11/1998 | Matsuda |
| 5,919,163 A | * | 7/1999 | Glickman .......... A61M 25/1011 604/101.05 |
| 5,947,985 A | | 9/1999 | Imran |
| 5,951,514 A | * | 9/1999 | Sahota .................... A61F 2/958 604/101.05 |
| 5,954,687 A | | 9/1999 | Baudino |
| 6,013,054 A | * | 1/2000 | Jiun Yan ........... A61M 25/1029 604/103.07 |
| 6,017,324 A | * | 1/2000 | Tu .......................... A61F 2/954 604/103.07 |
| 6,048,333 A | * | 4/2000 | Lennox ............. A61B 17/0057 604/101.01 |
| 6,071,285 A | * | 6/2000 | Lashinski ............... A61F 2/958 604/103.04 |
| 6,086,557 A | * | 7/2000 | Morejohn ............ A61M 1/3659 604/101.01 |
| 6,129,704 A | | 10/2000 | Forman et al. |
| 6,146,370 A | | 11/2000 | Barbut |
| 6,193,685 B1 | * | 2/2001 | Goodin ............. A61M 25/1006 604/102.01 |
| 6,223,637 B1 | | 5/2001 | Hansen |
| 6,296,655 B1 | | 10/2001 | Gaudoin et al. |
| 6,364,900 B1 | | 4/2002 | Heuser |
| 6,514,281 B1 | * | 2/2003 | Blaeser ..................... A61F 2/954 623/1.12 |
| 8,403,911 B2 | | 3/2013 | Garrison et al. |
| 8,460,240 B2 | | 6/2013 | Towler |
| 8,480,619 B2 | | 7/2013 | Porter |
| 8,496,629 B2 | | 7/2013 | McKinnon et al. |
| 8,747,456 B2 | * | 6/2014 | Baim ....................... A61F 2/958 623/1.35 |
| 8,951,226 B2 | | 2/2015 | Hameed |
| 8,956,383 B2 | | 2/2015 | Aklog |
| 9,295,818 B2 | | 3/2016 | Riina |
| 9,364,634 B2 | | 6/2016 | Adams et al. |
| 9,399,112 B2 | | 7/2016 | Shevgoor et al. |
| 9,440,043 B2 | | 9/2016 | Arora et al. |
| 9,579,494 B2 | | 2/2017 | Kersten et al. |
| 9,642,673 B2 | | 5/2017 | Adams et al. |
| 9,993,325 B2 | | 6/2018 | Ren |
| 10,299,824 B2 | | 5/2019 | Walzman |
| 10,328,246 B1 | | 5/2019 | Walzman |
| 10,314,684 B2 | | 6/2019 | Walzman |
| 10,576,245 B2 | | 3/2020 | Walzman |
| 2002/0052620 A1 | * | 5/2002 | Barbut .................. A61B 17/22 606/190 |
| 2002/0165572 A1 | * | 11/2002 | Saadat ............. A61B 17/12022 606/194 |
| 2002/0188276 A1 | | 12/2002 | Evans |
| 2003/0023204 A1 | | 1/2003 | Vo |
| 2003/0097169 A1 | * | 5/2003 | Brucker .................. A61F 2/856 623/1.11 |
| 2003/0198798 A1 | * | 10/2003 | Hehrlein ............... A61L 29/146 428/313.5 |
| 2004/0006306 A1 | | 1/2004 | Evans |
| 2004/0024347 A1 | | 2/2004 | Wilson |
| 2004/0059278 A1 | * | 3/2004 | McPherson ............ A61B 7/005 604/8 |
| 2004/0122465 A1 | * | 6/2004 | McMurtry .......... A61M 25/104 606/194 |
| 2005/0038420 A1 | * | 2/2005 | Huybregts ............... A61F 7/123 606/20 |
| 2005/0171505 A1 | * | 8/2005 | Bertolero ............... A61B 1/313 604/508 |
| 2006/0235459 A1 | * | 10/2006 | Das ........................ A61F 2/954 606/192 |
| 2007/0038170 A1 | * | 2/2007 | Joseph ................. A61M 1/3667 604/6.16 |
| 2007/0185445 A1 | | 8/2007 | Nahon |
| 2007/0197997 A1 | * | 8/2007 | Dua .................... A61M 25/1006 604/509 |
| 2007/0287967 A1 | * | 12/2007 | Hekmat ............... A61M 25/008 604/284 |
| 2008/0039786 A1 | | 2/2008 | Epstein |
| 2008/0125746 A1 | | 5/2008 | Shapland |
| 2008/0281394 A1 | | 11/2008 | Jones |
| 2009/0209855 A1 | | 8/2009 | Drilling |
| 2009/0209907 A1 | * | 8/2009 | Grata ................. A61M 25/0032 604/96.01 |
| 2011/0190727 A1 | * | 8/2011 | Edmunds ................. A61F 2/958 604/509 |
| 2011/0245802 A1 | * | 10/2011 | Hayman .......... A61B 17/00491 604/509 |
| 2011/0276023 A1 | * | 11/2011 | Leeflang ............... A61M 1/3496 604/500 |
| 2012/0029436 A1 | * | 2/2012 | Yassinzadeh .... A61B 17/12045 604/187 |
| 2012/0116352 A1 | * | 5/2012 | Rangi ............. A61B 17/12022 604/509 |
| 2012/0136242 A1 | * | 5/2012 | Qi ........................ A61B 5/026 600/424 |
| 2012/0302953 A1 | | 11/2012 | Don Michael |
| 2012/0316632 A1 | | 12/2012 | Gao |
| 2013/0158511 A1 | | 6/2013 | Aggerholm |
| 2013/0190796 A1 | | 7/2013 | Tilson et al. |
| 2014/0025151 A1 | | 1/2014 | Gao |
| 2014/0148751 A1 | | 5/2014 | Kassab et al. |
| 2015/0196303 A1 | * | 7/2015 | Seguin ............... A61M 25/1011 606/194 |
| 2016/0278783 A1 | | 9/2016 | Magee |
| 2016/0324668 A1 | | 11/2016 | Wallace et al. |
| 2017/0000493 A1 | | 1/2017 | Boehm |
| 2017/0007800 A1 | * | 1/2017 | Chao .................... A61M 1/3659 |
| 2017/0086860 A1 | | 3/2017 | Lee |

(56) References Cited

U.S. PATENT DOCUMENTS

| | | |
|---|---|---|
| 2018/0126130 A1 | 5/2018 | Nitzan et al. |
| 2018/0161552 A1 | 6/2018 | Larson |
| 2018/0229010 A1 | 8/2018 | Walzman |

* cited by examiner

TEMPORARY BYPASS BALLOON CATHETER

BACKGROUND OF THE INVENTION

Field of the Invention

This invention relates in general to medical equipment and procedures. In particular, the invention relates to balloon catheters for use in performing certain endovascular procedures. More particularly, the present invention pertains to balloon catheters with a bypass element.

Background Art

Temporary balloon occlusion has become a routine and medically accepted technique for the management of patients with aneurysms or intracranial or head/neck tumors. The use of temporary balloon occlusion is particularly useful for the management of patients with aneurysms or intracranial or head/neck tumors who will likely require prolonged intra-operative or permanent occlusion of the internal carotid artery (ICA).

Endovascular procedures are generally less invasive procedure than alternative procedures and are used to treat problems affecting the blood vessels, such as an aneurysm, which is a swelling or "ballooning" of the blood vessel. Typically, the surgery involves making a small incision near each hip to access the blood vessels.

Endovascular procedures replaced clipping surgery for many cerebral aneurysms because it was a less invasive therapeutic procedure. Additionally, it was found that endovascular treatment is often superior because cerebral aneurysms, also called brain aneurysms, are a cerebrovascular issue in which weakness in the walls of a cerebral artery causes localized dilation or ballooning in the blood vessel and can be managed without direct contact with the brain.

Endovascular embolization of intracranial aneurysms initially required the placement of coils via a micro-catheter into the lesion until no additional coils could be placed. Such a procedure resulted in thrombosis and elimination of the aneurysm from the circulation system. This procedure resulted in numerous interstices. Said interstices increase the risk of coil "compaction" and recurrence of aneurysm. In some cases such shortcomings can be surmounted by the use of high-viscosity Onyx liquid embolic material. Onyx is a trade name for a copolymer used for embolisation therapy, which involves the occlusion of blood vessels. It is a liquid embolic agent. Onyx is produced and sold by Medtronic. Onyx consists of Ethylene Vinyl Alcohol Copolymer, soluted in Dimethyl-Sulfoxide (DMSO). Depending on the desired character of the liquid, the concentration can be varied: For example, 6% EVOH (Ethylene Vinyl Alcohol is a copolymer of ethylene and vinyl alcohol that can be used to give additional oxygen and gas barrier properties) and has a trade name of Onyx 18) or 8% EVOH (trade name Onyx 34). In other cases such shortcomings can be surmounted by the use of intrasaccular web devices, hydrogels, or various combinations of these and/or other intrasaccular devices and materials.

More particularly, liquid embolic agent composed of an ethylene vinyl alcohol copolymer dissolved in the organic solvent dimethyl sulfoxide (DMSO) opacified with tantalum powder is used in Onyx. Once coming into contact with an ionic solution the DMSO dissipates and the Onyx solidifies into a spongy, cohesive material. A high viscosity form of Onyx material is now used for the occlusion of some intracranial aneurysms.

After introducing a micro-catheter into the aneurysm, the aneurysm is temporarily occluded by a balloon which reduces the risk of the copolymer exiting the aneurysm and entering the native circulation, and then a viscous forms of Onyx material is delivered to the aneurysm via the micro-catheter.

The prior art contains several catheters with a hole in addition to the end hole. Most of these are taught by twelve patents: U.S. Pat. No. 9,440,043 (Arora et al.); U.S. Pat. Nos. 9,399,112; 9,364,634; 8,496,629; 8,403,911; 6,223,637; 5,954,687; 5,800,407; 5,180,387; 4,970,926; 4,784,638; and 4,755,176.

However, most are designed to drain cerebrospinal fluid from the ventricular through a catheter that enters through a hole in the skull and would not be capable of injecting glue into an artery that enters through the femoral artery and is snaked up through blood vessels in the body. Additionally, the inventions described in said patents could be used to inject something directly into the brain and/or ventricle. However, they could not be used to inject something into an artery within the brain, or to provide a temporary arterial bypass. If it were introduced directly into the artery through the brain it would undoubtedly cause a life threatening bleed in the brain. The medical basis is that a catheter designed to be inserted directly into the brain has no possible role for an intravascular application.

Additionally, the structure of the devices taught by said twelve patent differs from the structure of the present invention. In particular, U.S. Pat. No. 9,440,043 which is a catheter having a tapered structure and balloon formed above a lower drainage hole differ from the present invention because it has a balloon which covers the distal end hole and the present invention does not. U.S. Pat. No. 9,399,112 is a catheter hole having an inclined trailing edge while the present invention does not have an angled side hole. U.S. Pat. No. 9,364,634 teaches an embedded co-extrusion for improving catheter hole array efficiency, whereas the present invention does not use co-extrusions. U.S. Pat. No. 8,496,629 is a catheter which uses staggered diffusion holes a flow breaking feature, the present invention does not require any flow breaking feature. Similarly, U.S. Pat. No. 8,403,911 uses diffusion side holes to improve catheter efficiency, while the present invention does not require any flow breaking feature, including diffusion side holes. U.S. Pat. No. 6,223,637 is a catheter side-wall hole cutting apparatus, whereas the present invention while capable of deploying a device to cut a catheter side-wall has neither a suction element nor a cutting element. U.S. Pat. No. 5,954,687 teach the use of a fluid reservoir, however the present inventions does not. U.S. Pat. No. 5,800,407 is a multiple hole epidural catheter which teaches the use of both permanently opened and permanently closed holes, whereas the present inventions uses holes which can be both opened and closed on a temporary basis in addition to holes which are permanently open. Furthermore, the present invention is designed for intravascular, not epidural use. U.S. Pat. No. 5,180,387 teaches the use of angled holes in a catheter with a non-circular bore, the present invention teaches non-angled holes in a circular bore.

U.S. Pat. No. 4,970,926 teaches an apparatus for making angled hole ventricular catheter which uses a plurality of rods with an end hole in each, where as the present invention teaches the use of side holes. The '638 shows is an angled hole ventricular catheter designed for extended impartment in the brain, whereas the present invention does not use angled holes and is not intended for extended impartment in the brain. U.S. Pat. No. 4,755,176 teaches a catheter with side hole in one of two lumens, whereas the present invention is a single lumen device.

The prior art teaches the use of balloons for flow control in endovascular treatments of target aneurysm. For example, see Moret J, Cognard C, Weill A, Castaings L, Rey A. reported in J Neuroradiol. 1997; 24:30-44 which focused on reconstruction technique in the treatment of wide-neck intracranial aneurysms.

The use of a temporary balloon occlusion is a standard operating procedure when it is desirable to block or closing a blood vessel. It is a medically accepted technique for the management of patients suffering from aneurysms or some intracranial or head/neck tumors. The deployment of a non-detachable silicone balloon catheter is routine to implement temporary a blood vessel closure. Existing, non-detachable silicone balloon catheters are composed of a type of "soft" catheter with an inflatable "balloon" at its tip. The deflated non-detachable silicone balloon catheter is positioned, then inflated to perform the necessary procedure, and deflated again in order to be removed.

The most significant difficulty associated with the use of occlusion balloons for endovascular treatment of aneurysms is the potential for ischemia in the vascular territory when blood flow is occluded by balloon inflations. Thus there is a need to facilitate continued blood flow after placement of a balloon.

This bypass balloon catheter could also allow the tamponading of a bleeding site in a vessel, caused by traumatic injury, iatrogenic injury, spontaneous rupture and/or other disease states, to be tamponaded for prolonged periods while minimizing the risk of ischemic injury to the vascular territory involved. Such temporary tamponade alone can stop the bleeding in some cases. In other cases, such tamponade can temporarily stop the bleeding, allowing additional time for the performance of additional endovascular or open surgical procedures to provide a permanent closure of the bleeding site.

SUMMARY OF INVENTION

Endovascular treatment of aneurysms with preservation of the parent artery continues to be difficult to implement. The present invention teaches a novel device and simple technique to deploy a balloon delivery catheter across a target aneurysm to facilitate a temporary bypass so as to improve the success rates for endovascular treatments of aneurysms with preservation of the parent artery and while minimizing risks of treatment.

The present invention teaches the use of a bypass element in the catheter to allow continued perfusion of the distal vascular territory while the balloon(s) is(are) inflating. The present invention provides a bypass element to allow continued perfusion of the involved vascular territory while simultaneously completely occluding the neck of an aneurysm with a balloon inflated across its neck, to facilitate treatment of the aneurysm. Furthermore, the device of the current invention has at least one proximal inflow "window" that can also allow delivery of micro-catheters and/or other therapeutic devices to facilitate treatment of such aneurysms.

The present invention also provides a bypass element to allow continued perfusion of the involved vascular territory while simultaneously allowing prolonged balloon inflations that can tamponade an actively bleeding vascular site.

The present invention is composed of a catheter with at least one distal end hole, at least one bypass window proximal to said end hole and a balloon element between said end hole and said bypass window. The present invention is capable of deploying said balloon element, before inflation, across the neck of a target aneurysm while simultaneously positioning said bypass windows proximally of said target aneurysm so as to allow a micro catheter to be pushed from the proximal end of said catheter, through said bypass window, around said balloon and into said target aneurysm. Said micro catheter once deployed is capable of delivering material into said target aneurysm. Once the micro-catheter is in its desired position, the balloon can be inflated to help facilitate the aneurysmal therapy.

Some versions can taper before the bypass windows as well, to allow more flow into the windows, the segment with the balloon can be bigger again or the smaller "tapered down size", or other variant. Some versions can branch after the proximal bypass "window(s)" to facilitate treatment of lesions at vessel-branching points.

DETAILED DESCRIPTION OF THE DRAWINGS

FIG. 4A is a perspective view of the proximal end of an alternative catheter of the current invention, depicting an embedded lumen within the catheter wall.

DETAILED DESCRIPTION OF THE INVENTION

Figure 1:
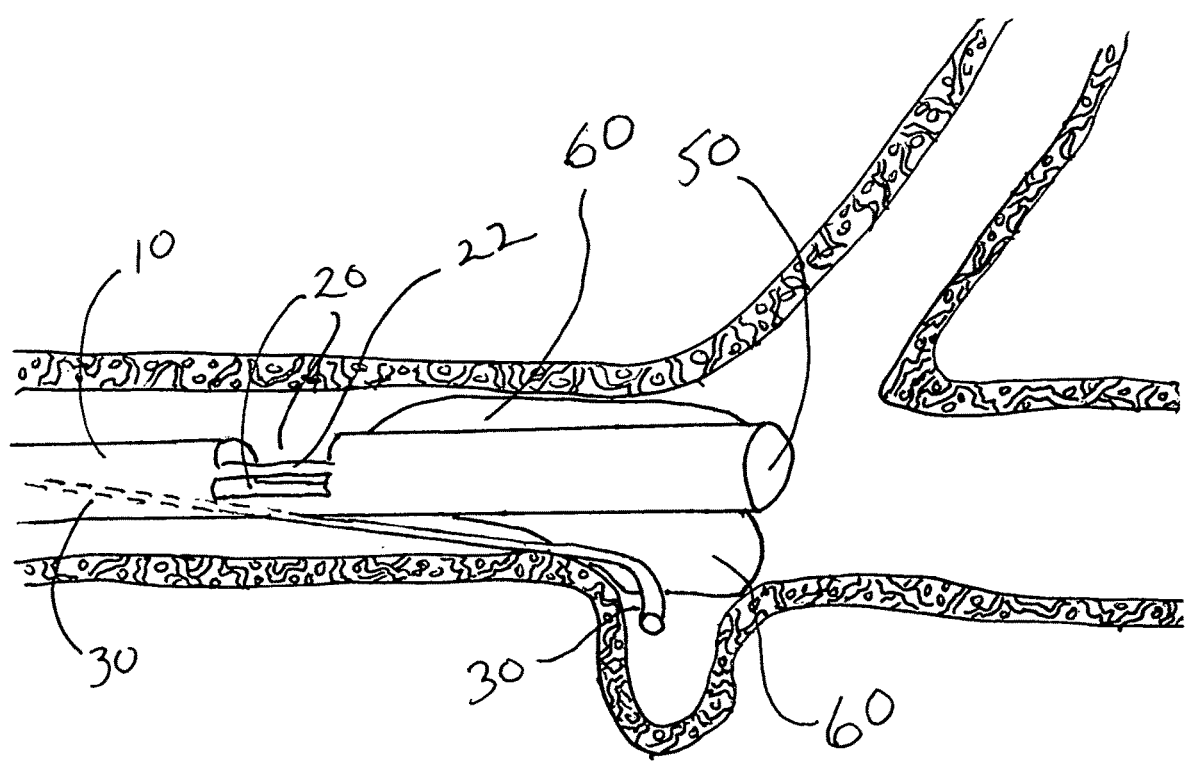
FIG. 1 is a perspective view of the catheter of the current invention disposed within a lumen across an aneurysm.

The present invention is composed of a catheter 10 with a distal end hole 50, at least one bypass window 20 proximal to said end hole 50 and a balloon 60 element between said end hole 50 and said bypass window 20. The present invention is capable of deploying said balloon 60 element across the neck of a target aneurysm (shown depending in cutaway profile) while simultaneously positioning said bypass windows 20 proximally of said target aneurysm so as to allow a micro-catheter 30 to be pushed from the proximal end of said catheter 10, through said bypass window 20, around said balloon 60 and into said target aneurysm. Said micro-catheter 30, once deployed, is capable of delivering material into said target aneurysm.

Referring now to FIG. 1, the preferred embodiment is composed of a balloon 60 mounted to a catheter 10 similar to a Merci/Concentric/Stryker Flowgate Balloon Guide Catheter. The present invention differs from the Merci/Concentric/Stryker Flowgate Balloon Guide Catheter in that it could not be a stiff guide. The present invention must be sufficiently flexible so as to be deliverable to distal brain anatomy. In this respect the present invention would incorporate elements of the penumbra Ace 060 5Max and 068 5Max Ace catheters, and the MicroVention Sofia catheters, but with a balloon 60 across the distal tip 50 region like the Flowgate, and bypass window(s) proximal to the balloon that allow inflow of blood flow for bypass during balloon inflations.

The present invention differs from all prior art due to the incorporation of at least one window element 20 in the catheter just proximal to a deployed balloon 60 element. Said window 20 may be a segment of the present invention's catheter 10 that is composed of two or more struts 22 resulting in one or more window(s) 20.

The present invention adds value to a surgeon because said surgeon can advance the balloon 60 across the neck of an aneurysm or across a bleeding site, then inflate the balloon 60. The balloon 60 tamponades the bleeding and/or allows delivery of coils with balloon 60 remodeling and/or allows "contained" delivery of liquid embolic (Onyx 500) and/or other intrasaccular treatment such as coils, hydrogel, or other intrasaccular therapy, and the balloon 60 does not have to be periodically deflated to allow distal brain perfusion. Instead the "windows" 20 in the catheter 10 proximal to the balloon 60 allow continuous flow of blood during inflation. The blood just flows into the windows 20, through the distal catheter 10 (the segment that has the balloon mounted to it), and out the distal tip 50 of the catheter.

Figure 4:
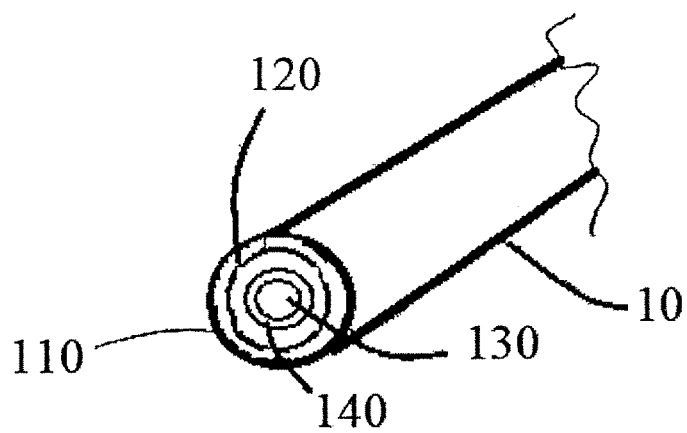
FIG. 4 is a perspective view of the proximal end of the catheter of the current invention, depicting an interior tube.
Figure 4:
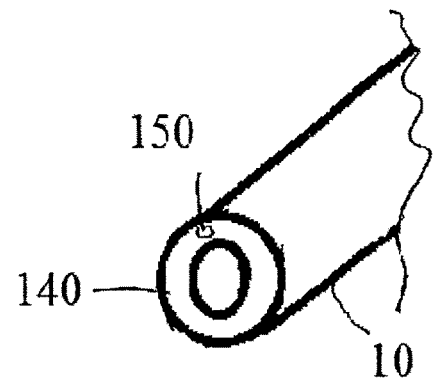

Referring now to FIG. 4, the catheter comprises a flexible external tubular wall 101 and an inner tube 140. Blood flows through the interior 130 of tube 140 to distal tip 50. A tubular lumen 120 starts at the proximal end of catheter 10 continuously through the proximal end of strut 22. Lumen 120 is capable of carrying material to inflate balloon 60. Flexible internal tubular wall 140 also starts at the proximal end of catheter 10 continuously through the proximal end of strut 22. Interior lumen 130 allows passage of a micro-catheter (not shown) to pass therethrough to the target aneurysm. Interior lumen 130 starts at the proximal end of catheter 10 continuously through the proximal end of strut 22.

Referring to FIG. 4A, in an alternate embodiment wherein said catheter 10 is composed of a tubular structure 140 having an embedded lumen 150. Embedded lumen 150 allows passage of a micro-catheter (not shown) to pass therethrough to the target aneurysm. Interior lumen 150 starts at the proximal end of catheter 10 continuously through the proximal end of strut 22.

In the embodiment of the current invention having a single window 20 bypass, channel 120 or embedded lumen 150 pass directly into balloon 60 element. In an alternate embodiment, additional lumens similar to embedded lumen 150 can be added. The additional lumen can be used for micro-catheters when the joint use of embedded lumen 150 for both balloon 60 inflations and deflations, and passage of a micro-catheter is not desirable.

In the preferred embodiment having a multiple windows 20 are connected by at least one hollow strut 22. In this embodiment, channel 120 or embedded lumen 150 connect through hollow strut 22 to allow flow of inflating material into balloon 60 element. In an alternate embodiment, at least a second window 20 is connected by at least one hollow strut 22. In this embodiment, channel 120 or embedded lumen 150 connect through hollow strut 22 to allow flow of inflating material into balloon 60 element.

Figure 5:
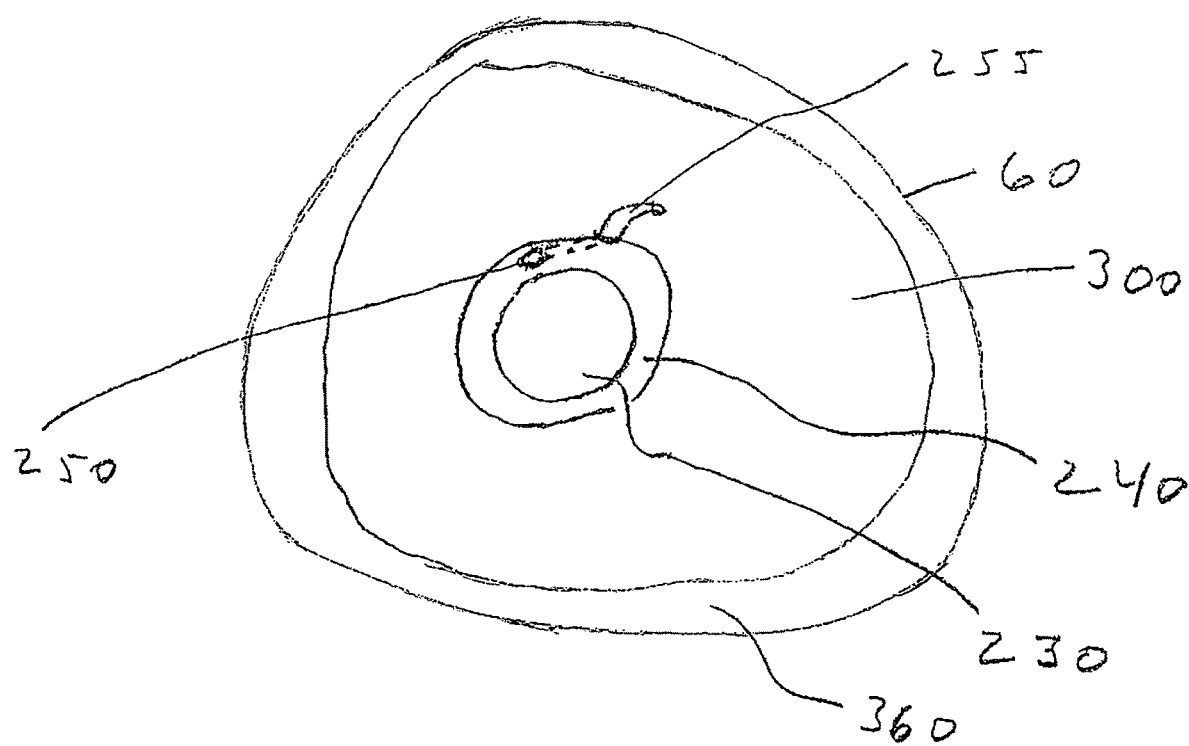
FIG. 5 is a cutaway view of the interior of the balloon element disposed on the distal end of the catheter proximal to the aneurysm/pathology to be treated.

Referring to FIG. 5, in the preferred embodiment, flexible tube balloon 60 element is disposed upon flexible tube 240. Within tube 240 is embedded lumen 250 corresponding with embedded lumen 150 to transport the inflating material. Embedded lumen 250 terminates at inflation/deflation nozzle 255. Nozzle 255 protrudes into inflation bladder 300 within the exterior wall 360 of balloon 60.

Figure 2:
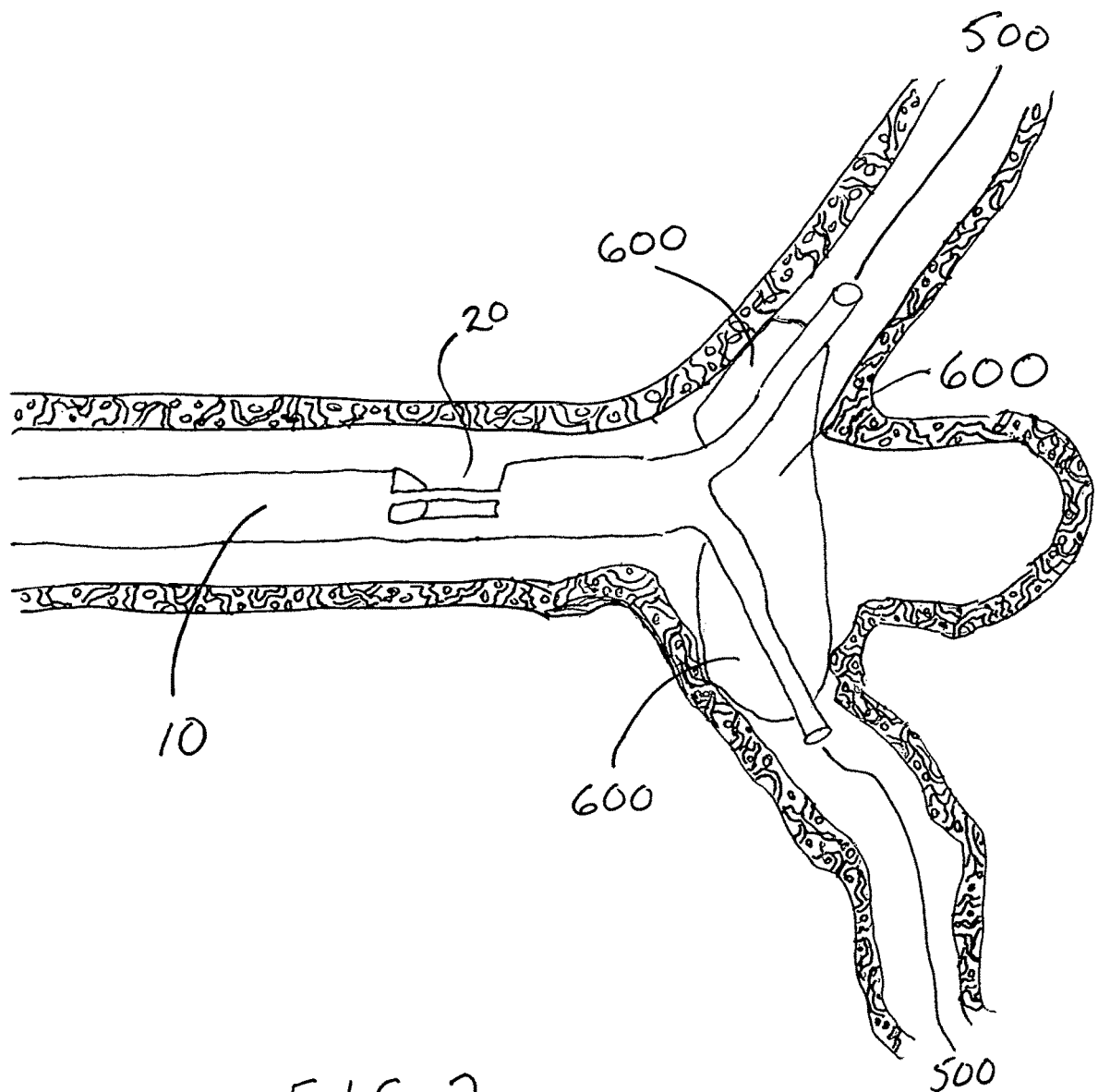
FIG. 2 is a perspective view of the catheter of the current invention having a branched balloon disposed within a lumen across a wide-neck aneurysm at the vascular branching point.

Referring now to FIG. 2, in some versions the catheter can also bifurcate or trifurcate (or more branches) after the window(s) 20, with a branched balloon 600 crossing the vascular branch point(s), to allow treatments of branch point aneurysms as well (with distal catheter lumen ending in all major branches). In this embodiment, the catheter 10 is bifurcated at branching point having at least one more end hole 500 for blood to flow around the target wide-neck aneurysm. A branched balloon 600 adapted for positioning within a vascular branching point is disposed near the distal end of said catheter 10.

Figure 3:
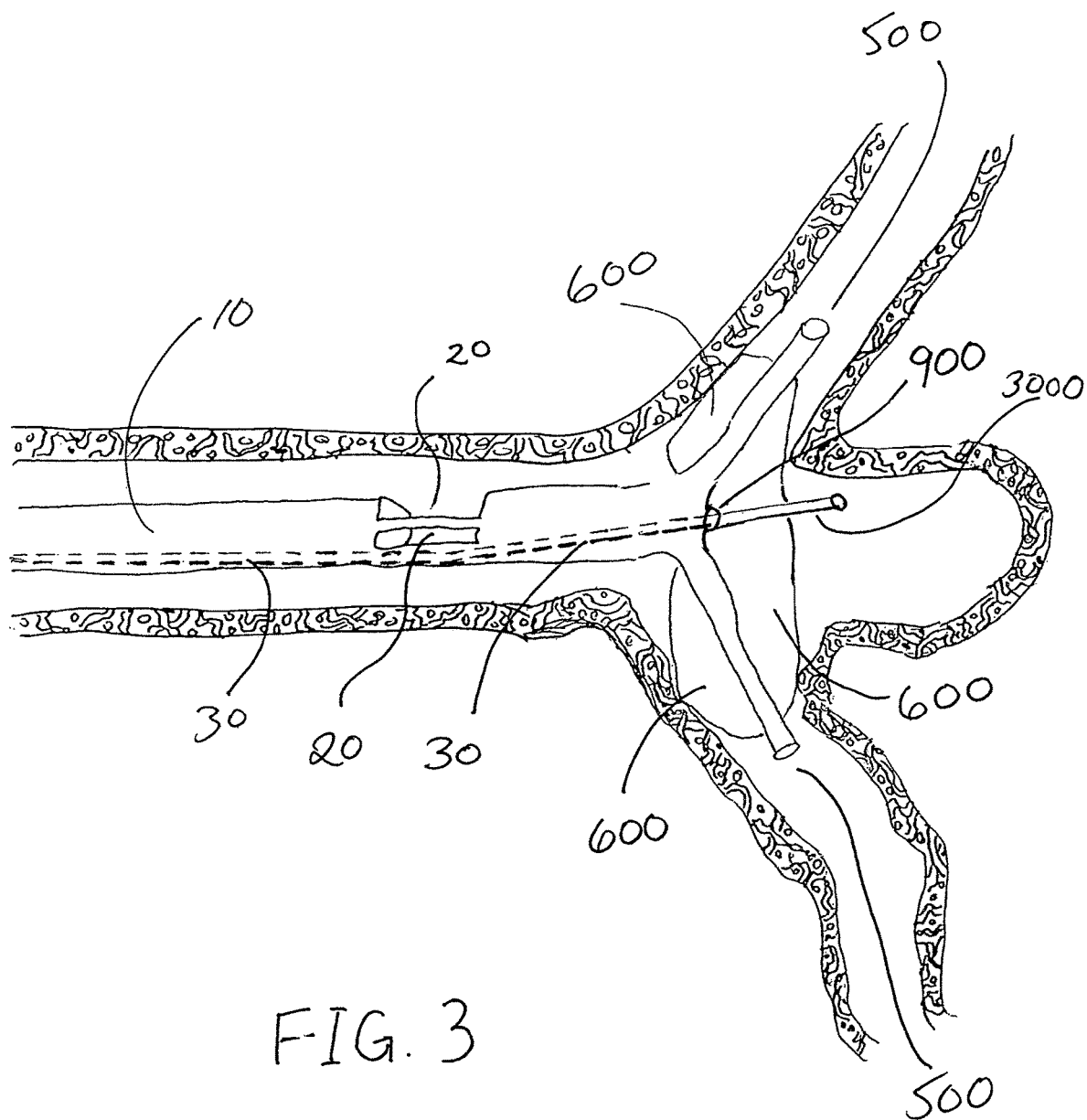
FIG. 3 depicts a perspective view of the embodiment of FIG. 2, further including a bifurcation hole disposed across a vessel branching point for a micro-catheter extension to pass through a branched balloon.

Referring now to FIG. 3, in another embodiment adapted to vascular branch-point treatment, incorporating all elements noted in FIG. 2, but having two additional elements. The first additional element is a bifurcation hole 900 disposed at the branch point of said branched balloon 600 to allow a micro-catheter to pass through said bifurcation hole 900 to treat a wide-neck aneurysm at the vascular branch point directly. The second optional, additional element is micro-catheter extension 3000. Micro-catheter extension 3000 allows faster and easier placement of micro-catheter 30 when a target aneurysm requires.

Additionally, the catheter element of the current invention can even be used simultaneously to access the aneurysm with another micro-catheter 30—with micro-catheter 30 going through the proximal end of catheter 10, then exiting the catheter 10 at a bypass window 20 to access the aneurysm/pathology.

The micro-catheter 30 is advanced over a microwire (not shown), which is soft and steerable. The operator has to steer the microwire in the correct direction. The micro-catheter 30 can be advanced and positioned when the balloon 60 is deflated. Then the microwire can be removed and the balloon 60 can be inflated.

In some non-limiting iterations of the bifurcation/branch point design a treatment micro-catheter with a single or dual lumen can be incorporated into the current device, coming out at the branch point(s). This iteration of the current invention will allow surgeons to ameliorate the adverse affects of targeted aneurysm more quickly, more accurately and at less cost than alternatives taught by prior art.

Figure 6:
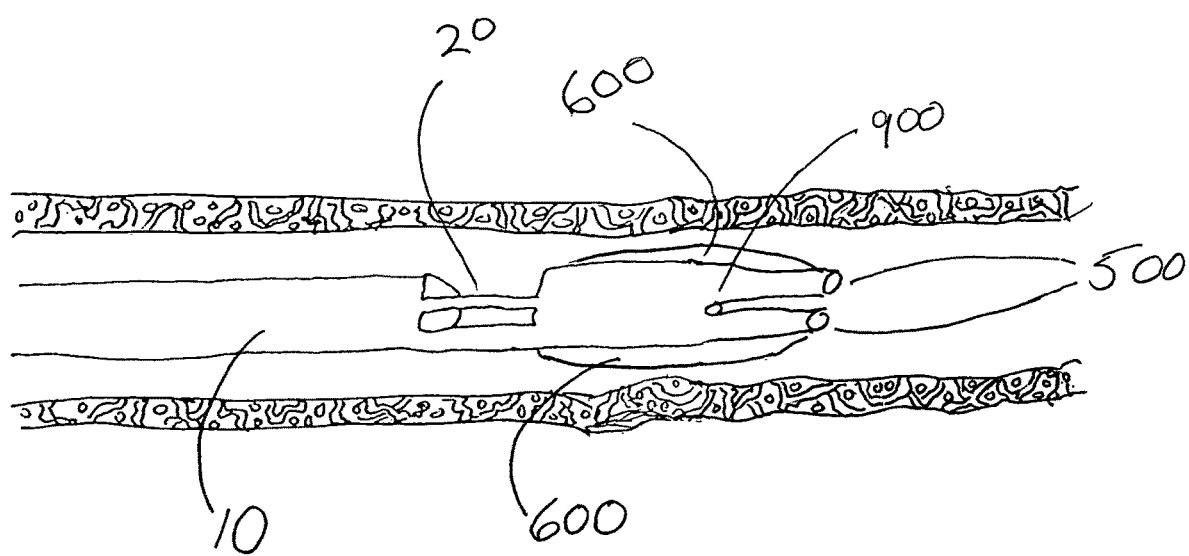
FIG. 6 is a view of the device of FIG. 2 before and after deployment within a vessel.

In some embodiments of the present invention, such as the bifurcated end hole of FIGS. 2, 3 and 6, there may be additional, separate elements that extend from the proximal hole of catheter 10 across the bypass window 20 ending at the branched balloon 600, thus resulting in at least two lumens. In the branched balloon 600 embodiment, an example of such an inner element includes a dual lumen dilation/introducer designed to line up with and marry to the two arms of the branched balloon 600 such that the branched balloon 600 may be introduced through a vessel over two separate wires. This embodiment would also incorporate separate holes within branched balloon 600 to allow wires passing through catheter 10 to guide each branch of branched balloon 600 into proper position. Additionally, in an alternative embodiment, the micro-catheter extension element 3000 is embedded into the device and can be steered over an independent wire into the target aneurysm.

In other non-limiting iterations of the present invention, various elements of the present invention can taper before the bypass windows too, to allow more flow into the windows 20. For example the segment with balloon 60 can be bigger again than the smaller "tapered down size", among other. For added support and stability some embodiments may have additional struts 22 and "windows" 20 distal to the balloon 60 as well to allow the blood flow back into the vessel, with continuing catheter 10 beyond that, that in many embodiments may taper to a smaller catheter size. Thus, the balloon 60 is "stabilized" more and less likely to have its position dislodged by blood flow.

Although the invention has been described in detail in the foregoing embodiments for the purpose of illustration, it is to be understood that such detail is solely for that purpose, and that variations can be made therein by those skilled in the art without departing from the spirit and scope of the invention, except as it may be described by the following claims.

I claim:

1. A catheter comprising:
an elongated tube,
   wherein said tube is configured to have:
      a proximal end and a distal end;
      at least one bypass window,
         wherein said at least one bypass window is configured to have at least two exits,
         wherein said at least two exits are divided by a strut;
         wherein said least one bypass window is located proximally to said distal end;
      at least one an end hole,
         wherein said end hole is located at said distal end;
      an inflatable balloon,
         wherein said balloon is disposed between a distal-most end of said at least one bypass window and said end hole; and
      at least two channels,
         wherein a first channel allows communication from said proximal end to said end hole while the balloon is inflated, and
         wherein a second channel allows communication from said proximal end to said balloon to communicate inflation material to said balloon,
         wherein said second channel extends from said proximal end,
         through said strut, to said balloon
      a bifurcation defining a first branch and a second branch;
      a second end hole located between said first branch and said second branch;
      wherein said bifurcation is disposed distally of said at least one bypass window,
      said balloon extending distally beyond said second end hole upon inflation:
      a micro-catheter which communicates with said proximal end, said at least one bypass window, and said vascular target;
      a bifurcation lumen in an inner wall of said tube suitable to allow said micro-catheter to pass through; and
      a micro-catheter extension exiting said balloon via said second end hole.

2. The catheter of claim 1, further comprising:
a micro-catheter that communicates with said proximal end, one of said at least one bypass window, and a vascular target,
wherein said vascular target is proximal to said balloon.

3. The catheter of claim 2, wherein said micro-catheter communicates with said proximal end and said distal end, and said end hole,
wherein said micro-catheter extends through said tube in parallel to said at least two exits in said at least one bypass window and said balloon.

4. The catheter of claim 2, wherein a distal end of said micro-catheter terminates simultaneously with said distal end.

5. A catheter comprising:
an elongated tube forming an outer member and defining a plurality of bypass windows separated by a strut, said elongate tube having a first elongated proximal segment proximal of the plurality of bypass windows and a second elongated distal segment distal of the plurality of bypass windows and in communication with the plurality of windows, a proximal end of the distal segment open to blood flow, the distal segment of the elongated tube including:
   a distal end hole;
   an inner lumen configured to communicate blood to said distal end hole; and
   a bifurcation in the distal segment of the elongated tube bifurcating the distal segment into a first branch and a second branch;
an inflatable balloon supported on the elongate tube distally of all of the plurality of bypass windows;
wherein the distal end hole is in the first branch and the second branch includes a distal end hole, the distal end holes allowing blood to flow around a vascular target, and further including an opening at the bifurcation between the first and second branches
wherein the catheter has only one inflatable balloon.

6. The catheter of claim 5, wherein the plurality of bypass windows are located proximally of the distal end hole.

7. The catheter of claim 5, wherein the inner lumen is configured for passage of a micro-catheter through the inner lumen such that the micro-catheter is extendable from the inner lumen through the at least one bypass window to thereby access a vascular target.

8. The catheter of claim 5, wherein the first and second branches of the distal segment are exposed to blood.

9. The catheter of claim 5, wherein the balloon is configured to circumscribe the first branch and the second branch and the catheter is devoid of balloons proximal of the plurality of bypass windows.

10. The catheter of claim 5, wherein the distal end hole is in the first branch and the catheter further comprises an opening located between the first branch and the second branch, the opening configured to allow a micro-catheter to pass therethrough.

11. The catheter of claim 10, wherein the balloon extends distally beyond the opening between the first branch and the second branch.

12. A catheter comprising:
a single tubular member, the tubular member including:
   an outer wall having a plurality of bypass windows formed therein; and
   a lumen configured to facilitate communication of blood therethrough;
a balloon supported on the tubular member distally of the plurality of bypass windows;
the single tubular member having a bifurcated segment forming a first branch and a second branch, the balloon spanning a gap between the first and second branches, wherein the balloon lacks a concave portion between the first and second branches.

13. The catheter of claim 12, wherein the bifurcated segment in is only in the tubular member and the balloon lacks a bifurcation.

14. The catheter of claim 12, wherein the catheter has a second lumen configured for passage of a micro-catheter through the second lumen such that the micro-catheter is extendable from the second lumen past the plurality of bypass windows to thereby access a vascular target.

15. The catheter of claim 12, wherein the first and second branches are exposed to blood.

16. The catheter of claim 12, wherein the first branch and the second branch each have an open distal end to allow blood to flow therethrough and around the vascular target and an opening is located between the first branch and second branch.

\* \* \* \* \*